United States Defensive Publication [19] (H) [11] T971,003

Orphanides [43] June 6, 1978

[54] SYNTHESIS OF DIMALEIMIDES

[75] Inventor: Gus George Orphanides, Newark, Del.

[73] Assignee: E. I. du Pont de Nemours and Company, Wilmington, Del.

[21] Appl. No.: 645,219

[22] Filed: Dec. 29, 1975

[51] Int. Cl.[2] ..... C07D 403/06; C07D 403/02

[52] U.S. Cl. ..... 260/326.26

[57] ABSTRACT

Bifunctional maleimides can be prepared in high yield by reacting an organic diamine with maleic anhydride in a solvent composed of the azeotrope of hexamethylphosphoramide or 1-methyl-2-pyrrolidone and acetic acid, followed by dehydration of the intermediate with acetic anhydride in the presence of an alkali metal salt of a $C_2$–$C_5$ aliphatic acid. The solvent systems are recoverable by reduced pressure distillation and can be used in subsequent syntheses of maleimides.

5 Claims, No Sheets Drawing,

12 Pages Specification

The file of this unexamined application may be inspected and copies thereof may be purchased (849 O.G. 1221, Apr. 9, 1968).